(12) United States Patent (10) Patent No.: US 9,408,974 B2
Pommereau et al. (45) Date of Patent: Aug. 9, 2016

(54) BUNG FOR DRUG CONTAINING CARTRIDGES IN DRUG DELIVERY DEVICES

(75) Inventors: Christian Pommereau, Frankfurt am Main (DE); Anke Liewald, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/321,492

(22) PCT Filed: May 20, 2010

(86) PCT No.: PCT/EP2010/056977
§ 371 (c)(1),
(2), (4) Date: Feb. 23, 2012

(87) PCT Pub. No.: WO2010/133675
PCT Pub. Date: Nov. 25, 2010

(65) Prior Publication Data
US 2012/0143147 A1   Jun. 7, 2012

(30) Foreign Application Priority Data

May 20, 2009   (EP) .................................... 09006821

(51) Int. Cl.
*A61M 5/315*   (2006.01)
(52) U.S. Cl.
CPC ....... *A61M 5/31511* (2013.01); *A61M 5/31525* (2013.01); *A61M 5/31573* (2013.01)

(58) Field of Classification Search
CPC ..................... A61M 5/31511; A61M 5/31525; A61M 5/31573
USPC ................. 604/218, 403, 220, 225–226, 229, 604/236–238
See application file for complete search history.

(56) References Cited

U.S. PATENT DOCUMENTS

| 2,607,342 | A | | 8/1952 | Abel | |
| 4,501,192 | A | * | 2/1985 | Knodel | ........................... 92/248 |
| 2003/0233075 | A1 | | 12/2003 | Huegli | |

(Continued)

FOREIGN PATENT DOCUMENTS

| DE | 10226643 A1 | 1/2004 |
| EP | 0743072 A2 | 11/1996 |

(Continued)

OTHER PUBLICATIONS

European Patent Application Examination Report issued in European Patent Application No. 10723072.4 dated Feb. 3, 2016.

*Primary Examiner* — Rebecca E Eisenberg
(74) *Attorney, Agent, or Firm* — McDonnell Boehnen Hulbert & Berghoff LLP

(57) ABSTRACT

The present invention relates to a bung (20) for drug containing cartridges (10) for use in drug delivery devices wherein the bung (20) has a distal end face (22), a proximal end face (24) and a lateral area (26), wherein the bung (20) comprises at least two different materials, a first material (30) covering the whole lateral area (26) of the bung (20) and a second material (32) which is at least partly arranged inside the bung (20), wherein the first material (30) has a larger compressibility than the second material (32) and wherein the whole lateral area (26) has a flat surface. Furthermore, it relates to a cartridge (10) and to a drug delivery device comprising a bung (20) as claimed.

15 Claims, 1 Drawing Sheet

(56) References Cited

U.S. PATENT DOCUMENTS

2005/0101920 A1* 5/2005 Keane et al. .................. 604/218
2007/0219507 A1  9/2007 Dai et al.
2007/0219508 A1* 9/2007 Bisegna et al. ............... 604/218

FOREIGN PATENT DOCUMENTS

GB           578827       7/1946
WO       2005099793 A1   10/2005

* cited by examiner

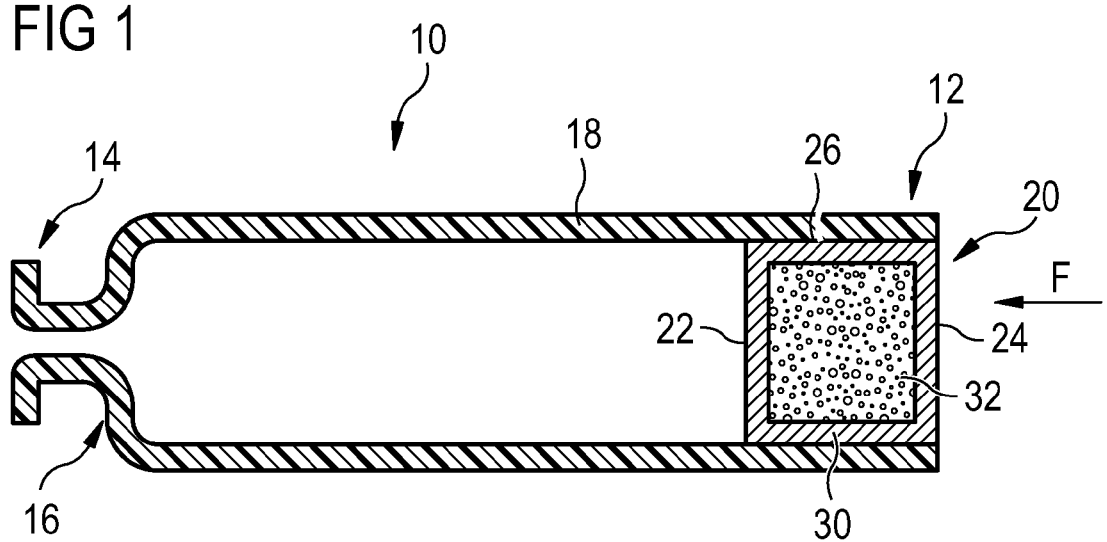
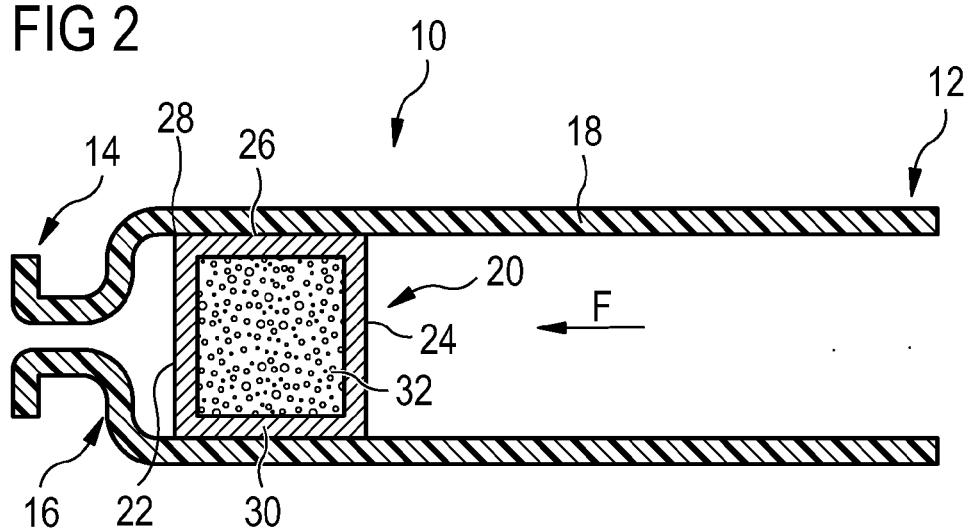

BUNG FOR DRUG CONTAINING CARTRIDGES IN DRUG DELIVERY DEVICES

CROSS REFERENCE TO RELATED APPLICATIONS

The present application is a 35 U.S.C. 371 National Application of PCT/EP2010/056977 filed May 20, 2010, which claims priority to European Patent Application No. 09006821.4 filed May 20, 2009, the entire contents of which are incorporated entirely herein by reference.

The present invention relates to a bung for drug-containing cartridges for use in drug delivery devices.

Drug delivery devices are generally known for the administration of a drug, for example insulin, but also for other medicinal products for self-administration by a patient.

Because of the daily necessity to use these drug delivery devices, there are ambitions to make the use of these drug delivery devices more comfortable and safer for the user. An endeavor in this field is to avoid dose inaccuracy while dispensing the last dose from the cartridge. Some examples to solve this problem are known from WO 2005/099793 A1 and from US 2007/0219507 A1.

It is an object of the present invention to provide a bung for drug-containing cartridges for use in drug delivery devices which helps to avoid dose inaccuracy.

According to a first aspect of the disclosure, a bung for drug-containing cartridges for use in drug delivery devices is provided wherein the bung has a distal end face, a proximal end face and a lateral area, wherein the bung comprises at least two different materials, a first material covering the whole lateral area of the bung and a second material which is at least partly arranged inside the bung, wherein the first material has a larger compressibility than the second material and wherein the whole lateral area has a flat surface.

The bung is intended for sealing the proximal end of a cartridge by forming a liquid-proof closure between the lateral area of the bung and a main body portion of the cartridge. For this purpose the bung comprises two materials, a first material which is softer and a second material which is harder than the first material.

The first material is covering the whole lateral area of the bung and due to the relatively high compressibility of the first material the bung is able to adapt its shape to the shape of the main body portion of the cartridge. Furthermore it is preferred that the first material is chosen such that the bung is enabled to be easily slided by a piston in axial direction along the main body portion. The bung is driven forward, by mechanical contact between the piston and the bung.

The second material is at least partly arranged inside the bung and provides a rigid core to resist or at least to limit axial compression of the bung while a piston is pressed onto the bung and is applying a force in distal direction.

In a preferred embodiment the second material comprises metal.

The second material which is at least partly arranged inside the bung can comprise metal. This metal can be pure metal or an alloy.

An alloy is herein after understood as a mixture of two or more elements in which the major component is a metal. Metals can be shaped by processes such as casting, extrusion, sintering and machining.

To be more specific with casting, molten metal is poured into a shaped mould. With extrusion, a hot and malleable metal is forced under pressure through a die, which shapes it before it cools. With sintering, a powdered metal is compressed into a die at high temperature. With machining, lathes, milling machines, and drills cut the cold metal to shape.

According to another preferred embodiment the second material comprises ceramic.

Ceramic forming techniques are for example injection moulding, dry pressing, and other variations.

With injection moulding, liquid ceramic is filled into a mould. With dry pressing, ceramic powder is pressed in mechanical or hydraulic powder compacting presses.

In one embodiment the second material comprises a polymer matrix.

In case that both the first and the second material comprise a polymer a polymer with a smaller compressibility than the first material is used as second material. The material used as second material has a longer chain length than the first material in order to decrease the compressibility. By varying the chain length of the polymer materials the strength and toughness of the materials can be modulated. Crosslinking, like vulcanization also increases strength and toughness of the material.

By increasing the chain length, the chain interactions also increase and therefore the Van-der-Waals-attractions and entanglements increase. The chains are held more strongly in position and resist deformations. The result is that the matrix breaks up at higher stresses and higher temperatures. Besides the chain length having an influence in the properties of a polymer there is another influence given by the fact that a polymer is branched or unbranched. Basically, the more branched a polymer is, the tighter is the polymer.

In another preferred embodiment, the first material comprises rubber.

Materials that may be considered for coating the surface are, for example, silicone rubber and acrylic rubber. All elastomers are conceivable for being used as first material.

In another preferred embodiment the first material of the bung arranged at the lateral area enables the bung, together with the shape of the bung, to seal a proximal end of a drug-containing cartridge.

The surface material should almost completely resist to being dissolved in the drug contained in the cartridge and particularly, very few monomers should be dissolved if the surface material is a polymer. There should also be only low abrasion with the cartridge while the bung is axially displaced for dispensing the drug.

In a preferred embodiment the first material of the bung covers the distal end face of the bung.

By covering the distal end face and the lateral area of the bung, it is possible to have a consistent surface structure in the lateral area and at the distal end face of the bung which is easy to manufacture.

In a particularly preferred embodiment the distal end face of the bung has a flat surface.

This flat surface is advantageous to increase the dose accuracy while dispensing the last dose from the medicament cartridge wherein dose means a certain volume of a liquid medicinal product. For dispensing the last dose of the drug, the bung is moved forward by the mechanical contact with a piston in a drug delivery device.

Near the distal end of the cartridge, an edge of the distal end face of the bung abuts a shoulder portion of the cartridge and the bung comes to a stop. While abutting this shoulder portion, the first material, in particular the first material at the edge of the distal end face, is compressed in axial direction.

By having a flat surface and a constant and thin layer thickness at the distal end face of the bung, it is possible to have a constant compression at the distal end face of the bung while abutting the shoulder portion of the cartridge.

In another preferred embodiment the first material covers the whole surface of the bung.

To manufacture such a bung comprising at least two different materials, there are many processes that can be used. One example is the sandwich process. There are two melts which are successively die-casted into a cavity by means of a mixing head. The resulting structure is a core-shell structure in case that only two melts are used, or a multi-layer structure in case that more than two melts are used.

In a further preferred embodiment the bung comprises a core and a layer coating the core wherein the layer comprises the first material and the core comprises the second material.

By having a thin layer coating the core of the bung the compression of the bung is reduced and thus the bung has also a reduced retention time after compression. This compression results from the pressure of the piston exerted on the bung while the medicinal product is dispensed from the cartridge.

In a particularly preferred embodiment the bung is manufactured by injection molding.

One advantage of injection molding is that hard/soft material combinations can be processed at the same time by multi-component injection molding.

In another preferred embodiment a cartridge comprises a main body portion, a shoulder portion and a bung wherein the bung is moveable along a longitudinal axis within the main body portion of the cartridge.

The texture of the surface material of the bung should enable the bung to be slideable with respect to the cartridge.

In another preferred embodiment the bung abuts the shoulder portion of the cartridge being located at the distal end of the cartridge while expelling the last dose of the medicament from the cartridge.

After dispensing the most of the medicinal product through, for example an adapted needle unit, at the distal end of the cartridge, the bung abuts a narrowing shoulder portion of the cartridge. At this position the bung comes to a stop.

Another aspect of the present invention is a drug-delivery device comprising a cartridge and a piston rod actuating a bung. The bung can be axially displaced by a piston.

By having a bung as it is described here, the drug delivery device is able to dispense a more precise dose of the medicinal product. This is achieved by reduced relaxation times of the bung and more accurate dispensing of the last possible dose of a medicinal product contained in the cartridge.

In another preferred embodiment a drug delivery device comprises a bung that abuts the shoulder portion being located at the distal end of the cartridge while expelling the last dose of the medicinal product from the cartridge.

In the following the invention is described in further detail with reference to the drawings, wherein FIG. 1 shows a cross sectional view of a cartridge comprising a bung at a first position at the proximal end of the cartridge, and FIG. 2 shows a cross sectional view of a cartridge comprising a bung at a second position at the distal end of the cartridge while the bung abuts a narrowing shoulder portion of the cartridge.

Some preferred embodiments of the cartridge and the bung according to the present invention will now be discussed with reference to FIG. 1 and FIG. 2. Identical reference signs denote identical or comparable components.

In FIG. 1 a cross sectional view of a cartridge 10 comprising a bung 20 at a first position is shown. At this position the bung 20 is located at the distal end of the cartridge 14. The cartridge 10 has a main body portion 18, a narrowing shoulder portion 16 and contains a liquid medicinal product.

In this position of the bung 20 it is possible to push the bung 20 in a distal direction by applying a force F onto the bung 20. This can be achieved by a piston, which is not shown in FIG. 1, located at the proximal end of the cartridge 12.

The bung 20 shown in FIG. 1 comprises two different materials and the surface of the bung comprises a lateral area 26, a distal end face 22 and a proximal end face 24. The lateral area 26 of the bung 20 contacts the main body portion 18 of the cartridge 10.

In FIG. 1 a first material 30 which is covering the whole surface of the bung 20, and a second material 32 forming a core which is covered by the first material 30 is shown.

The first material 30 has a higher compressibility and is pressed against the inner wall of the main body portion 18 of the cartridge 10 and is therefore able to form a fluid-proof sealing for the medicinal product contained in the cartridge 10.

In FIG. 2 a cross sectional view of a cartridge 10 Comprising a bung 20 in a second position is shown. In this position the bung 20 abuts a narrowing shoulder portion 16 of the cartridge 10 and is compressed. While applying pressure onto the bung 20 by a piston which is not explicitly shown, the first material 30 at the edge of the distal end face 28 is compressed while abutting the narrowing shoulder portion 16.

Due to the special structure, the compression is limited by the layer thickness of the first material 30 at the distal end face of the bung and by the low compressibility of the second material 32 inside the bung 20. By having a flat surface structure at the lateral area 26 of the bung 20, the first material 30 located at the lateral area 26 is not squeezed in proximal direction while being pushed towards the narrowing shoulder portion 16. Due to this, the dose accuracy is increased and the retention time of the bung 20 after compression is decreased.

If the first material 30 did not have a flat surface structure but a lamellar structure there would be a low resistivity against deformation of the bung 20 while abutting the narrowing shoulder portion 16 of the cartridge 10. By applying the same force onto a bung with lamellar structure and to a bung 20 with a flat surface structure, the deformation of a lamellar structure is stronger.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14, Trp(O2)25, IsoAsp28] Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence H-(Lys)6-des Pro36 [Asp28] Exendin-4(1-39)-Lys6-NH2, des Asp28 Pro36, Pro37, Pro38 Exendin-4(1-39)-NH2, H-(Lys)6-des Pro36, Pro38 Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

REFERENCE NUMERALS 10 cartridge
12 proximal end of the cartridge
14 distal end of the cartridge
16 shoulder portion
18 main body portion
20 bung
22 distal end face
24 proximal end face
26 lateral area
28 edge of the distal end face
30 first material
32 second material
F force

The invention claimed is:

1. A bung for drug containing cartridges for use in drug delivery devices wherein the bung has
   a distal end face,
   a proximal end face
   and a lateral area,
   wherein the bung comprises at least two different materials, a first material covering the whole lateral area of the bung and a second material which is entirely arranged inside the first material of the bung and seamlessly covered by the first material,
   wherein the first material has a larger compressibility than the second material
   wherein the whole distal end face of the bung has a flat surface
   wherein the whole lateral area has a flat surface, and
   wherein the bung is manufactured by injection molding.

2. A bung according to claim 1, wherein the second material comprises metal.

3. A bung according to anyone of the previous claims, wherein the second material comprises ceramic.

4. A bung according to claim 1, wherein the second material comprises a polymer matrix.

5. A bung according to claim 1, wherein the first material comprises rubber.

6. A bung according to claim 1, wherein the first material arranged at the lateral area together with the shape of the bung enables the bung to seal a proximal end of a drug containing cartridge.

7. A bung according to claim 1, wherein the first material covers the distal end face of the bung.

8. A bung according to claim 1, wherein the first material covers the whole surface of the bung.

9. A bung according to claim 1, wherein the bung comprises a core and a layer coating the core, wherein the layer comprises the first material and the core comprises the second material.

10. A cartridge comprising a main body portion, a shoulder portion and a bung according to claim 1, wherein the bung is moveable along a longitudinal axis within the main body portion of the cartridge.

11. A cartridge according to claim 10, wherein the bung abuts the shoulder portion being located at the distal end of the cartridge while expelling the last dose of the medicament from the cartridge.

12. A drug delivery device comprising a cartridge according to claim 10 and a piston rod actuating the bung.

13. A drug delivery device comprising a cartridge with a bung according to claim 11, wherein the bung abuts the shoulder portion being located at the distal end of the cartridge while expelling the last dose of the medicament from the cartridge.

14. A bung according to claim 1, wherein the first material has a constant and thin layer thickness.

15. A bung for drug containing cartridges for use in drug delivery devices wherein the bung has
- a distal end face,
- a proximal end face
- and a lateral area,
- wherein the bung comprises at least two different materials, a first material covering the whole lateral area of the bung and a second material which is entirely arranged inside the first material of the bung and seamlessly covered by the first material,
- wherein the first material has a larger compressibility than the second material
- wherein the whole distal end face of the bung has a flat surface, and
- wherein the whole lateral area has a flat surface.

* * * * *